United States Patent [19]

Demetre

[11] Patent Number: 4,988,511
[45] Date of Patent: Jan. 29, 1991

[54] INSECTICIDAL PASTE INCLUDING POWDERED BORIC ACID

[76] Inventor: Margaret K. Demetre, 9602 Highmeadow, Houston, Tex. 77063

[21] Appl. No.: 529,596

[22] Filed: May 29, 1990

Related U.S. Application Data

[63] Continuation-in-part of Ser. No. 428,984, Oct. 30, 1989, abandoned, which is a continuation-in-part of Ser. No. 103,996, Feb. 18, 1988, abandoned.

[51] Int. Cl.$^5$ ..................... A01N 25/08; A01N 25/00
[52] U.S. Cl. ........................................ 424/84; 424/410
[58] Field of Search .......................... 424/84, 445, 410

[56] References Cited

U.S. PATENT DOCUMENTS

| | | | |
|---|---|---|---|
| 2,177,598 | 10/1939 | Herzig | 424/84 |
| 3,496,272 | 2/1970 | Kruger | 424/410 |
| 4,049,460 | 9/1977 | Broadbent | 514/89 |
| 4,386,071 | 5/1983 | Carbe | 424/724 |
| 4,438,090 | 3/1984 | Brite | 424/148 |
| 4,826,682 | 5/1989 | Sakhorava | 424/84 |
| 4,834,977 | 5/1989 | Kohama | 424/405 |

FOREIGN PATENT DOCUMENTS

| | | | |
|---|---|---|---|
| 1185172 | 4/1985 | Canada . | |
| 1233115 | 10/1960 | France | 424/84 |
| 7223198 | 1/1969 | Japan | 424/84 |
| 59-067209 | 4/1984 | Japan . | |
| 1078705 | 4/1986 | Japan | 424/148 |
| 5705 | of 1896 | United Kingdom | 424/148 |

OTHER PUBLICATIONS

Chem. Abst. 107:213625x (1987).
Chem. Abst. 92:175789r (1980).
Chem. Abst. 105:129478c (1986).
Chem. Abst. 91:205659x (1979).
Chem. Abst. 105:221038y (1986).
Chem. Abst. 66:10171z (1967).

Primary Examiner—Douglas W. Robinson

[57] ABSTRACT

An insecticidal paste that adheres, hardens and remains on hard surfaces in hidden and out of the way places and is composed in a delicately balanced combination of a mixture of sugar, milk solids, butter fat, water and a green pigment of liquid food coloring with a powdered form of boric acid in 100 to 400 mesh keeping away all others indefinitely.

3 Claims, No Drawings

INSECTICIDAL PASTE INCLUDING POWDERED BORIC ACID

RELATED APPLICATION

This application is a continuation-in-part of my earlier filed U.S. patent application Ser. No. 07/428,984 filed Oct. 30, 1989 now abandoned which is a continuation-in-part of U.S. Ser. No. 07/130,996 filed Feb. 18, 1989, now abandoned.

DESCRIPTION OF PREFERRED EMBODIMENTS

This invention is an insecticidal paste directed to the specific combination of the simple and preferred sweetner sugar, milk solids, butter fat, water and a green pigment of liquid food coloring and boric acid in the powdered form of 100 to 400 mesh.

It has been found that the sugar, milk, solids, butter fat, water and the green pigment of liquid food coloring are compatible with boric acid in this balanced combination and are not affected by water or moisture or by weather or humidity as this paste becomes rock-hard after application.

It has been found that the balanced combination of sugar, milk solids, butter fat, water and the green pigment of liquid food coloring together with the boric acid in this insecticidal paste triggers the boric acid in eliminating roaches immediately. This delicately balanced combination kills all trapped roaches and goes on working as a repellent keeping away all others. A one year warranty is stated on label.

Further, it has been found that the balanced combination of the particular and specific components in this insecticidal paste comprised the boric acid, sugar, milk solids, butter fat, water and the green food coloring do not enhance survival by boosting the immune system by fortifying with a variety of nutrients specifically these of whole grains as to cause the survival of most roaches.

The method of preparation of this insecticidal paste is made by combining the sugar, milk solids, butter fat and water and bringing to a boil of up to two minutes and then allowing the mixture to cool to a room-temperature syrup before blending in the boric acid and the food coloring to a smooth, thick paste. The syrup preserves the boric acid and keeps it working continuously killing and repelling and keeping away all roaches indefinitely.

Preferably, this insecticidal paste comprises 56% by weight boric acid in the powdered form of 100 to 400 mesh, sugar 14% by weight, milk solids 7% by weight, butter fat 3% by weight, water 19% by weight and a green pigment of liquid food coloring 1% by weight.

Further, it is preferred that the liquid pigment of green food coloring is this formula be of a substance used in food so as not to adversely affect the formulas. Although the color, green gives this insecticidal paste a foreboding appearance adverse consumption is not likely as this non-residual formula is applied behind and under hard surfaces such as appliances and low-leg furniture where it adheres, hardens and remains and therefore, out of the reach of children and pets.

Because a second application is rarely necessary in this insecticidal paste a one year money-back warranty is stated on the label.

I claim:

1. An insecticidal paste composition in a delicately balanced formula comprised of about 56% by weight of boric acid in the powdered form of 100 to 400 mesh, 14% by weight sugar, 7% by weight milk solids, 3% by weight butter fat, 19% by weight water and 1% by weight of a liquid food coloring pigment.

2. A method of preparing the insecticidal paste of claim 1 comprising combining the sugar, milk solids, butter fat and water, bringing the mixture to a boil for up to two minutes and then allowing the mixture to cool to a room temperature syrup, then blending in the boric acid and food coloring pigment to form a thick, smooth paste.

3. The method of killing and controlling roaches comprising applying to an infested area an insecticidally effective amount of the composition of claim 1.

* * * * *